(12) United States Patent
Ottosen

(10) Patent No.: US 6,303,641 B1
(45) Date of Patent: Oct. 16, 2001

(54) CYANOAMIDINES AS CELL PROLIFERATION INHIBITORS

(75) Inventor: Erik Rytter Ottosen, Ølstykke (DK)

(73) Assignee: Leo Pharmaceuticals Products Ltd., Ballerup (DK)

( * ) Notice: Subject to any disclaimer, the term of this patent is extended or adjusted under 35 U.S.C. 154(b) by 0 days.

(21) Appl. No.: 09/424,581

(22) PCT Filed: May 15, 1998

(86) PCT No.: PCT/DK98/00198

§ 371 Date: Nov. 26, 1999

§ 102(e) Date: Nov. 26, 1999

(87) PCT Pub. No.: WO98/54147

PCT Pub. Date: Dec. 3, 1998

(30) Foreign Application Priority Data

May 29, 1997 (GB) .................................... 9711126

(51) Int. Cl.⁷ .......................... A61K 31/44; C07D 213/36
(52) U.S. Cl. ............................. 514/357; 546/330
(58) Field of Search .............. 514/357; 546/330

(56) References Cited

FOREIGN PATENT DOCUMENTS 94 06770   3/1994  (WO) .
061559  * 10/2000  (WO) .

OTHER PUBLICATIONS

Schou et al., Bioorganic and medicinalChemistry Letter, vol. 7, No. 24, p. 3095–3100.*

Nakajima et al: "Cyanoamidines. I. Synthesis and vasodilatory activity of substituted heteroaromatic cyanoamidines", Chemical and Pharmaceutical Bulletin., vol. 42, No. 12, 1994, pp. 2475–2482, XP00207917.

Nakajima et al: "Cyanoamidines. II. Synthesis and pharmacological activity of N–arylalkyl–N'–cyano–3–pyridinecarboxamidines", Chemical and Pharmaceutical Bulletin., vol. 42, No. 12, 1994, pp. 2384–2490 XP002079718.

* cited by examiner

Primary Examiner—Jane Fan
(74) Attorney, Agent, or Firm—Pillsbury Winthrop LLP

(57) ABSTRACT

Compounds of the following formula are used for inhibiting cell proliferation:

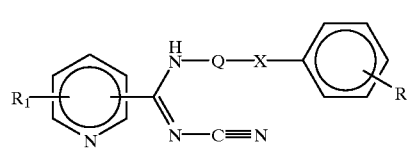

wherein R, R1, Q, X are as defined in the specification.

6 Claims, No Drawings

CYANOAMIDINES AS CELL PROLIFERATION INHIBITORS

This application is the national phase of international application PCT/DK98/00198 filed May 15, 1998 now WO 98/54147; which designated the U.S.

This invention relates to a hitherto unknown class of compounds which shows strong activity in inhibiting undesirable cell proliferation in e.g. skin cells and cancer cells, to pharmaceutical preparations containing these compounds, to dosage units of such preparations, and to their use in the treatment and prophylaxis of diseases characterized by abnormal cell differentiation and/or cell proliferation such as e.g. psoriasis and cancer.

The compounds of the present invention are represented by the general formula I

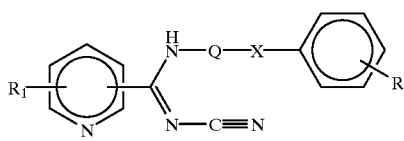

or their tautomeric forms, the attachment to the pyridine being in the 2-, 3- or 4-position, in which formula $R_1$ stands for one or more substituents which can be the same or different and are selected from the group consisting of: hydrogen, halogen, amino, trifluoromethyl, nitro, cyano, carboxy, or alkyl, alkoxy, or alkoxycarbonyl, the C-content of which can be from 1 to 4; Q stands for $C_4$–$C_9$ divalent hydrocarbon radical which can be straight, branched, saturated or unsaturated; X stands for methylene, oxygen, sulphur or nitrogen, and R stands for hydrogen or for one or more substituents which can be the same or different and are selected from the group consisting of: hydroxy, amino, halogen, trifluoromethyl, cyano, nitro, carboxy, carbamoyl, methylenedioxy, or alkyl, alkoxy, alkylthio, alkylamino, or alkoxycarbonyl, the C-content of which can be from 1 to 4.

If the present compounds contain one or more asymmetric carbon atoms, these compounds may form optical isomers or diastereoisomers. The present invention also comprises such isomers, and mixtures of same.

The compounds can be used in the form of their salts which are formed with pharmaceutically acceptable inorganic or organic acids, such as hydrochloric, hydrobromic and hydroiodic acid, phosphoric acid, sulphuric acid, nitric acid, 4-toluenesulphonic acid, methanesulphonic acid, formic acid, acetic acid propionic acid, citric acid, tartaric acid, succinic acid, benzoic acid, and maleic acid and lithium, sodium, potassium, magnesium, calcium salts, as well as salts with ammonia, C1–C6-alkylamines, C1–C6 alkanolamines, procaine, cycloalkylamines, benzylamines, and heterocyclic amines.

Even if the present compounds are well absorbed after enteral administration, in some cases it can be advantageous to prepare suitable bioreversible derivatives of compounds of the invention, i.e. to prepare so-called prodrugs, preferably derivatives, the physicochemical properties of which leads to improved solubility at physiological pH and/or absorption and/or bioavailability of the compound in question.

Such derivatives are for instance pyridyl N-oxide derivatives of compounds of the invention, such compounds being prepared by oxidation of the pyridyl N by a suitable oxidising agent, e.g. with 3-chloroperbenzoic acid in an inert solvent, e.g. dichloromethane.

Other suitable methods to improve the physicochemical properties and/or solubility of the compounds concerned can be used as well.

N-Alkyl-N'-cyano-N"-pyridylguanidines, described in United Kingdom Patent No. 1,489,879, are potent potassium channel activators with a pronounced effect as pre-capillary vasodilators, reducing the total peripheral resistance in animals and in man, and are thus useful as antihypertensives. The same biologically activity has been reported for a series of closely related N-alkyl-N'-cyano-pyridine-carboxamidines (Nakajima, T. et al, Chem. Pharm. Bull., 42 2475–2490, (1994), and U.S. Pat. No. 5,223,508). As stated in International Patent No. PCT/DK93/00291, filing date Sep. 13, 1993, Publication No. WO 94/06770 the introduction of aryloxy-containing radicals into the aliphatic groups from the above-cited U.K. Patent has led to structures showing more specific pharmacological effects on isolated tissues and cells and with no or a negligible effect on $^{86}$Rb-efflux from potassium channels, as compared with the established effect of compounds covered by the above-mentioned U.K. Patent.

The compounds of the present invention inhibit the proliferation of various tumour cell lines in cultures at a similar concentration as the best compounds from prior art (see table 1). However, the compounds of the present invention prolong the survival time of tumour-bearing rats significantly better, as compared to prior art, thus making them potentially useful in antineoplastic chemotherapy.

The inhibition of tumour cell proliferation was studied using different types of human cancer cell lines. The cell lines under investigation were small cell lung carcinoma (NYH), and breast cancer (MCF-7) using the following general procedure.

The cells were cultured in vitro for 24 hours in the presence of the compound under investigation. DNA synthesis was measured by incorporation of [3H]thymidine, and the median inhibitory concentrations ($IC_{50}$) of the compounds were calculated. Results are shown in Table 1.

TABLE 1

Inhibition of tumour cell proliferation in vitro in human small cell lung carcinoma (NYH) and human breast cancer (MCF-7) by compounds of the following examples of the present invention

| | The median inhibition concentration ($IC_{50}$, nM) of | |
|---|---|---|
| Compound from | NYH | MCF-7 |
| Example no. 1 | 39 | 350 |
| Example no. 2 | 340 | 540 |
| Example no. 3 | 350 | 740 |
| Prior art A | not tested | 10000 |
| Prior art B | 380 | 920 |
| Prior art C | 45 | 250 |

A: $N^2$-Cyano-$N^1$-octyl-3-pyridinecarboxamidine, Chem. Pharm. Bull., 42, 2475–2490, (1994)
B: N-Cyano-N'-(4-phenoxybutyl)-N"-4-pyridylguanidine, example 14 in PCT/DK93/00291
C: N-Cyano-N'-(5-phenoxypentyl)-N"-4-pyridylguanidine, example 18 in PCT/DK93/00291

The results show that the compounds of the present invention are able to inhibit the proliferation of tumour cells in vitro at the same or comparable concentrations than known compounds from prior art (see table 1).

The prolongation of survival time of tumour-bearing rats was studied in LEW/Mol inbred female rats inoculated with Yoshida sarcoma cells in a number of $2\times10^7$ cells. Tumour-bearing rats (6 animals per group) were dosed orally once daily from day 3 after the transfer of tumour cells and until death or until the body-weights had increased by 10% as a consequence of tumour proliferation. The mean survival day of treated versus non-treated rats is used to calculate ILS (Increased Life Span). ILS=((mean treated/mean control)−1)*100%. Results are shown in Table 2.

TABLE 2

Survival of Yoshida tumour-bearing rats treated with the compound of the Example no. 1 of the present invention

| Treatment | Compound | Dose (mg/kg, p.o.) | Increased life span (ILS)# % |
|---|---|---|---|
| None | — | — | 0.0¤ |
| Compound from the present invention | Example No. 1 | 10 | 60 |
|  |  | 20 | 90 |
|  |  | 30 | 102 |
| prior art C |  | 50 | 35 |

ILS = ((mean treated/mean control)-1)*100%
¤Untreated tumour carrying animals die between day 7 and 9
C: N-Cyano-N'-(5-phenoxypentyl)-N''-4-pyridylguanidine, example 18 in PCT/DK93/00291

These results show that the compounds of the present invention are able to prolong the survival time of Yoshida sarcoma tumour-bearing rats at lower concentrations and with higher ILS than the compound in example 18 in the PCT/DK93/00291.

The compounds of the invention are well tolerated and non-toxic and are exerting the described beneficial activities with no or minimal effect on the systemic blood pressure. In general, they may be administered by oral, intravenous, intraperitoneal, intranasal or transdermal routes.

The present invention also relates to methods for preparing the desired compounds of the general formula I. The compounds of the formula I may conveniently be prepared by standard procedures detailed in the art. The routes are outlined in the following reaction scheme.

Notes to scheme 1
a) Methanol, 20° C., 1–24 hours (see general procedure 1)

The present compounds are intended for use in pharmaceutical compositions which are useful in the treatment of the above mentioned diseases.

The amount required of a compound of formula (I) (hereinafter referred to as the active ingredient) for therapeutic effect will, of course, vary both with the particular compound, the route of administration and the mammal under treatment. A suitable dose of a compound of formula (I) for systemic treatment is 0.1 to 400 mg per kilogram bodyweight, the most preferred dosage being 1.0 to 100 mg per kg of mammal bodyweight, for example 5 to 20 mg/kg; administered once or more times daily.

A daily dose (for adults) may amount to 1 mg to 10000 mg, preferably from 70–5000 mg, and in the veterinary practice correspondingly in daily doses from 0.1 to 400 mg/kg bodyweight.

While it is possible for an active ingredient to be administered alone as the raw chemical, it is preferable to present it as a pharmaceutical formulation. Conveniently, the active ingredient comprises from 0.1% to 99% by weight of the formulation. Conveniently, dosage units of a formulation contain between 0.5 mg and 1 g of the active ingredient. For topical administration, the active ingredient preferably comprises from 1% to 20% by weight of the formulation but the active ingredient may comprise as much as 50% w/w. Formulations suitable for nasal or buccal administration may comprise 0.1% to 20% w/w. for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefor and optionally other therapeutic ingredient (s). The carrier(s) must be "acceptable" in the sense of being Scheme 1
Synthesis of the compounds of the general formula I

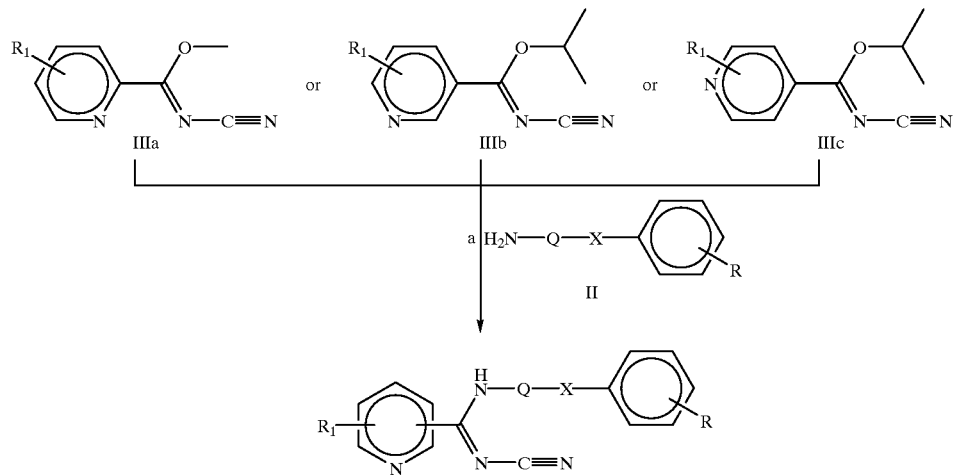

$R_1$, Q, X, and R are defined as compounds of the general formula I compatible with the other ingredients of the formulations and not deleterious to the recipient thereof.

The formulations include those in a form suitable for oral, rectal, parenteral (including subcutaneous, intramuscular, intravenous and intraperitoneal) administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carder such as cocoa butter, or in the form of an enema.

Formulations suitable for parenteral administration conveniently comprise a sterile oily or aqueous preparation of the active ingredient which is preferably isotonic with the blood of the recipient.

In addition to the aforementioned ingredients, the formulations of this invention may include one or more additional ingredients, such as diluents, buffers, flavoring agents, binders, surface active agents, thickeners, lubricants, preservatives, e.g. methylhydroxybenzoate (including antioxidants), emulsifying agents and the like.

The compositions may further contain other therapeutically active compounds usually applied in the treatment of the above mentioned pathological conditions, e.g. antineoplastic agents which may result in synergistic effects on tumour cells.

The invention will now be further described in the following general procedures and examples:

The exemplified compounds I are listed in table 3.

All melting points are uncorrected. For $^{13}C$ nuclear magnetic resonance (NMR) spectra (300 MHz) chemical shift values ($\delta$) are quoted, unless otherwise specified, for deuteriochloroform ($CDCl_3$) and hexadeuterodimethylsulfoxide (DMSO-$d_6$) solutions relative to internal tetramethylsilane ($\delta 0.00$) or chloroform ($\delta 76.81$ ($^{13}C$ NMR)). Chromatography was performed on silica gel.

TABLE 3

Exemplified compounds of general formula I.

| Comp. No. | Example No. | 2, 3 or 4 pyridyl | $R_1$ | Q | X | R |
|---|---|---|---|---|---|---|
| 101 | 1 | 3 | H | $(CH_2)_6$ | O | 4-Cl |
| 102 | 2 | 3 | H | $(CH_2)_6$ | O | 2-$OCH_3$ |
| 103 | 3 | 3 | H | $(CH_2)_6$ | O | 3, 4-$OCH_2O$ |
| 104 | 4 | 3 | H | $(CH_2)_6$ | O | 2, 4, 6-tri-Cl |
| 105 | 5 | 3 | H | $(CH_2)_6$ | O | 4-F |
| 106 | 6 | 3 | H | $(CH_2)_6$ | O | 3, 5-di-$OCH_3$ |
| 107 | 7 | 3 | H | $(CH_2)_6$ | O | 3-Cl |
| 108 | 8 | 3 | H | $(CH_2)_6$ | O | 2-$NO_2$ |
| 109 | 9 | 3 | H | $(CH_2)_6$ | O | 2-Cl |

TABLE 3-continued

Exemplified compounds of general formula I.

| Comp. No. | Example No. | 2, 3 or 4 pyridyl | $R_1$ | Q | X | R |
|---|---|---|---|---|---|---|
| 110 | 10 | 3 | H | $(CH_2)_6$ | O | 2, 3-di-Cl |
| 111 | 11 | 3 | H | $(CH_2)_6$ | O | 4-Cl, 3-$CH_3$ |
| 112 | 12 | 3 | H | $(CH_2)_8$ | $CH_2$ | H |
| 113 | 13 | 3 | H | $(CH_2)_4$ | O | H |
| 114 | 14 | 3 | H | $(CH_2)_7$ | O | 4-Cl |
| 115 | 15 | 3 | H | $(CH_2)_5$ | O | 4-Cl |
| 116 | 16 | 2 | H | $(CH_2)_6$ | O | 4-Cl |
| 117 | 17 | 4 | H | $(CH_2)_6$ | O | 4-Cl |

General procedure 1

Coupling of Compounds of the General Formula II with Compounds of the General Formula IIIa. IIIb, or IIIc to Compounds of the General Formula I A compound with the general formula IIIa, IIIb, or IIIc (5 mmol) was dissolved in methanol (10 ml) and a compound with the general formula II (10 mmol) in methanol (10 ml) was added. The reaction mixture was stirred at room temperature for typically 18 hours. The reaction mixture was evaporated in vacuo to afford the crude product. The crude product was further purified, e.g. by crystallization or flash chromatography to yield the title compound.

EXAMPLE 1

$N^2$-Cyano-$N^1$-(6(4-chlorophenoxy)hexyl)-3-pyridinecarboxamidine (Compound 101)

General procedure: 1

Starting compound II: 6-(4-Chlorophenoxy)hexylamine

Starting compound IIIb: Isopropyl N-cyano-3-pyndinecarboxyimidate

Purification: Chromatography using methanol/dichloromethane 1:20 as eluant followed by trituration in diethyl ether Mp: Sublimates at 69° C.; $^{13}C$ NMR ($CDCl_3$): $\delta$ 168.0, 157.6, 152.5, 147.5, 135.3, 129.3, 128.7, 125.4, 123.6, 117.1, 115.8, 68.0, 42.9, 29.0, 28.3, 26.6, 25.7.

EXAMPLE 2

$N^2$-Cyano-$N^1$-(6-(2-methoxyphenoxy)hexyl)-3-pyridinecarboxamidine (Compound 102)

General procedure 1

Starting compound II: 6(2-Methoxyphenoxy)hexylamine

Starting compound IIIb: Isopropyl N-cyano-pyndinecarboxyimidate

Purification: Chromatography using methanol/dichloromethane 1:20 as eluant followed by trituration in diethyl ether Mp: 87–88° C.; $^{13}C$ NMR ($CDCl_3$): $\delta$ 167.9, 152.4, 149.3, 148.4, 147.6, 135.2, 128.7, 123.5, 121.1, 121.0, 117.2, 113.3, 112.0, 68.8, 55.9, 42.8, 28.9, 28.1, 26.5, 25.6.

EXAMPLE 3

N$^2$-Cyano-N$^1$-(6-(3,4-methylenedioxyphenoxy)hexyl)-3-pyridinecarboxamidine (Compound 103)

General procedure 1
Starting compound II: 6-(3,4-Methylenedioxyphenoxy)hexylamine
Starting compound IIIb: Isopropyl N-cyano-3-pyrdinecarboxyimidate
Purification: Chromatography using methanol/dichloromethane 1:20 as eluant followed by crystallization from methanol
Mp: 130–131° C.; $^{13}$C NMR (DMSO-d$_6$): δ 167.7, 154.0, 151.9, 147.8, 147.7, 140.9, 135.4, 128.6, 123.4, 117.3, 107.9, 105.5, 100.8, 97.6, 68.0, 41.9, 28.5, 27.5, 26.0, 25.1.

EXAMPLE 4

N$^2$-Cyano-N$^1$-(6-(2,4,6-trichlorophenoxy)hexyl)-3-pyridinecarboxamidine (Compound 104)

General procedure 1
Starting compound II: 6-(2,4,6-Trichlorophenoxy)hexylamine
Starting compound IIIb: Isopropyl N-cyano-3-pyridinecarboxyimidate
Purification: Chromatography using ethyl acetate as eluant followed by crystallization from chloroform/diethyl ether
$^{13}$C NMR (DMSO-d$_6$): δ 167.7, 152.0, 150.2, 147.7, 135.5, 129.3, 128.8, 128.6, 123.4, 117.3, 73.5, 41.9, 29.3, 27.5, 26.0, 24.9.

EXAMPLE 5

N$^2$-Cyano-N$^1$-(6-(4fluoroghenoxy)hexyl)-3-pyridinecarboxamidine (Compound 105)

General procedure 1
Starting compound II: 6-(4-Fluorophenoxy)hexylamine
Starting compound IIIb: Isopropyl N-cyano3-pyridinecarboxyimidate
Purification: Chromatography using dichloromethanel/methanol /ammonia(aq.) 95:5:1 as eluant
Mp: 99–101° C.; $^{13}$C NMR (DMSO-d$_6$): δ 167.8, 157.9, 154.9, 154.7, 153.2, 152.3, 152.0, 147.8, 135.5, 128.6, 123.4, 117.3, 115.8, 115.6, 115.5, 115.5, 67.8, 41.9, 28.5, 27.5, 26.0, 25.1.

EXAMPLE 6

N$^2$-Cyano-N$^1$-(6-(3,5-dimethoxyohenoxy)hexyl)-3-pyridinecarboxamidine (Compound 106)

General procedure 1
Starting compound II: 6-(3,5Dimethoxyphenoxy)hexylamine
Starting compound IIIb: Isopropyl N-cyano-3-pyridinecarboxyimidate
Purification: Chromatography using dichloromethane/methanol /ammonia(aq.) 95:5:1 as eluant
$^{13}$C NMR (DMSO-d$_6$): δ 167.7, 161.1, 160.5, 152.0, 147.7, 135.4, 128.6, 123.4, 117.3, 93.1, 92.7, 67.3, 55.0, 41.9, 28.5, 27.5, 26.0, 25.1.

EXAMPLE 7

N$^2$-Cyano-N$^1$-($^6$-($^3$-chlorophenoxy)hexyl)3-pyridinecarboxamidine (Compound 107)

General procedure 1
Starting compound II: 6-(2-Chlorophenoxy)hexylamine
Starting compound IIIb: isopropyl N-cyano-3-pyridinecarboxyimidate
Purification: Chromatography using dichloromethanel/methanol /ammonia(aq.) 95:5:1 as eluant followed by trituration in diethyl ether
Mp: 77–79° C.; $^{13}$C NMR (DMSO-d$_6$): δ 167.7, 159.6, 152.0, 147.8, 135.5, 133.7, 130.7, 128.6, 123.4, 120.2, 117.3, 114.3, 113.5, 67.7, 41.9, 28.3, 27.5, 26.0, 25.1.

EXAMPLE 8

N$^2$-Cyano-N$^1$-(6(2-nitrophenoxy)hexyl-3-pyridinecarboxamidine (Compound 108)

General procedure 1
Starting compound II: 6-(2-Nitrophenoxy)hexylamine
Starting compound IIIb: Isopropyl N-cyano-3-pyridinecarboxyimidate
Purification: Chromatography using dichloromethane/methanol /ammonia(aq.) 95:5:1 as eluant followed by trituration in diethyl ether
Mp: 103–106° C.; $^{13}$C NMR (DMSO-d$_6$): δ 167.9, 152.1, 151.3, 147.9, 139.7, 135.6, 134.4, 128.8, 124.9, 123.5, 120.4, 117.4, 115.1, 69.1, 42.1, 28.3, 27.7, 26.0, 25.0.

EXAMPLE 9

N$^2$-Cyano-N$^1$-(6-(2-chlorophenoxy)hexyl)-3-pyridinecarboxamidine (Compound 109)

General procedure 1
Starting compound II: 6-(2-Chlorophenoxy)hexylamine
Starting compound IIIb: Isopropyl N-cyano-3-pyridinecarboxyimidate
Purification: Chromatography using dichloromethane/methanol /ammonia(aq.) 95:5:1 as eluant followed by trituration in chloroform/diethyl 1:4
Mp: 108–109° C.; $^{13}$C NMR (DMSO-d$_6$): δ 167.9, 154.0, 152.1, 147.9, 135.6, 129.9, 128.7, 128.3, 123.5, 121.4, 121.3, 117.4, 113.9, 68.4, 42.0, 28.4, 27.7, 26.1, 25.2.

EXAMPLE 10

N$^2$-Cyano-N$^1$-(6-(2,3dichlorophenoxy)hexyl)-3-pyridinecarboxamidine (Compound 110)

General procedure 1
Starting compound II: 6-(2,3-Dichlorophenoxy)hexylamine
Starting compound IIIb: Isopropyl N-cyano3-pyridinecarboxyimidate
Purification: Crystallization from methanol
Mp: 141–142° C.; $^{13}$C NMR (DMSO-d$_6$): δ 167.7, 155.5, 152.0, 147.8, 135.5, 132.2, 128.6, 128.4, 123.4, 121.8, 120.0, 117.3, 112.2, 69.0, 41.9, 28.3, 27.5, 25.9, 25.0.

EXAMPLE 11

N$^2$-Cyano-N$^1$-(6-(4-chloro-3-methylphenoxy)hexyl)
3-pyridinecarboxamidine (Compound 111)

General procedure 1
Starting compound II: 6-(4-Chloro-3-methylphenoxy)
  hexylamine
Starting compound IIIb: Isopropyl N-cyano3-
  pyridinecarboxyimidate
Purification: Chromatography using dichloromethanel/
  methanol /ammonia(aq.) 95:5:1 as eluant followed by
  trituration in diethyl ether
Mp: 91–92° C.; $^{13}$C NMR (CDCl$_3$): δ 167.9, 157.5, 152.4,
147.6, 136.9, 135.2, 129.5, 128.6, 125.6, 123.5, 117.2,
117.0, 113.0, 67.9, 42.8, 29.1, 28.3, 26.6, 25.7, 20.3.

EXAMPLE 12

N$^2$-Cyano-N$^1$-(9-phenylnonyl)-3-
pyridinecarboxamidine (Compound 112)

General procedure 1
Starting compound II: 9-Phenylnonylamine
Starting compound IIIb: Isopropyl N-cyano-3-
  pyridinecarboxyimidate
Purification: Chromatography using dichloromethane/
  methanol /ammonia(aq.) 90:10:1 as eluant followed by
  trituration in pentane
Mp: 54–57° C.; $^{13}$C NMR (CDCl$_3$): δ 167.9, 152.5, 147.5,
142.8, 135.3, 128.7, 128.4, 128.2, 125.6, 123.5, 117.1, 43.0,
36.0, 31.5, 29.4, 29.3, 29.2, 28.4, 26.9.

EXAMPLE 13

N$^2$-Cyano-N$^1$-(4-phenoxybutyl)-3-
pyridinecarboxamidine (Compound 113)

General procedure 1
Starting compound II: 4-Phenoxybutylamine
Starting compound IIIb: Isopropyl N-cyano-3-
  pyridinecarboxyimidate
Purification: Chromatography using dichloromethane/
  methanol /ammonia(aq.) 90:10:1 as eluant $^{13}$C NMR
  (CDCl$_3$): δ 168.0, 158.6, 152.5, 147.6, 135.2, 129.6,
  128.7, 123.5, 121.0, 117.2, 114.5, 67.2, 42.6, 26.6,
  25.3.

EXAMPLE 14

N2-Cyano-N$^1$-(7-(4-chlorophenoxy)heptyl)-3-
pyridinecarboxamidine (Compound 114)

General procedure 1
Starting compound II: 7-(4-Chlorophenoxy)heptylamine
Starting compound IIIb: Isopropyl N-cyano-3-
  pyridinecarboxyimidate
Purification: Chromatography using methanol/
  dichloromethane 1:20 as eluant
$^{13}$C NMR (DMSO-d$_6$): δ 167.7, 157.4, 152.0, 147.7,
135.4, 129.1, 128.6, 123.9, 123.4, 117.3, 116.1, 67.7, 42.0,
28.4, 28.3, 27.5, 26.2, 25.3.

EXAMPLE 15

N$^2$-Cyano-N$^1$-(5-(4chlorophenoxy)pentyl-3-
pyridinecarboxamidine (Compound 115)

General procedure 1
Starting compound II: 5-(4-Chlorophenoxy)pentylamine
Starting compound IIIb: Isopropyl N-cyano-3-
  pyridinecarboxyimidate
Purification: Chromatography using methanol/
  dichloromethane 1:20 as eluant
$^{13}$C NMR (DMSO-d$_6$): δ 167.8, 157.4, 152.0, 147.7,
135.4, 129.1, 128.6, 124.0, 123.4, 117.3, 116.1, 67.6, 41.8,
28.1, 27.3, 22.8.

EXAMPLE 16

N$^2$-Cyano-N$^1$-(6(4-chlorophenoxy)hexyl)-2-
pyridinecarboxamidine (Compound 116)

General procedure 1
Starting compound II: 6-(4-Chlorophenoxy)hexylamine
Starting compound IIIa: Methyl N-cyano-2-
  pyridinecarboxyimidate
Purification: Trituration in methanol and diethyl ether
Mp: 80–81° C.; $^{13}$C NMR (CDCl$_3$): δ 160.7, 157.7, 148.5,
147.3, 137.9, 129.3, 126.9, 125.4, 123.1, 116.8, 115.8, 68.0,
42.2, 29.3, 29.0, 26.5, 25.7.

EXAMPLE 17

N$^2$-Cyano-N$^1$-(6(4-chlorophenoxy)hexyl)-4-
pyridinecarboxamidine (Compound 117)

General procedure 1
Starting compound II: 6-(4-Chlorophenoxy)hexylamine
Starting compound IIIc: Isopropyl N-cyano-4-
  pyridinecarboxyimidate
Purification: Trituration in methanol and diethyl ether
Mp: 117–118° C.; $^{13}$C NMR (DMSO-d$_6$): δ 168.0, 157.5,
150.2, 139.6, 129.1, 124.0, 121.6, 116.9, 116.1, 67.7, 41.8,
28.4, 27.5, 26.0, 25.1.

EXAMPLE 18

| Capsules 1 Capsule contains: | |
|---|---|
| N$^2$-Cyano-N$^1$-(6-(4-chlorophenoxy)hexyl)-3-pyridine-carboxamidine (active compound) | 100 mg |
| Polyethylene Glycol | 962 mg |
| Gelatine Capsule no. 00 | |
| Gelatine | 122 mg |

EXAMPLE 19

| | Tablet Manufacture of 10,000 tablets | |
|---|---|---|
| I | N$^2$-Cyano-N$^1$-(6-(4-chlorophenoxy)hexyl)-3-pyridine-carboxamidine (active compound) | 10,000 kg |
| | Crosscarmellose sodium | 0,300 kg |
| II | Hydroxypropylmethyl cellulose, low viscosity type | 0,200 kg |
| | Sorbimacrogol oleate | 0,010 kg |
| | Purified water | q.s. |
| III | Crosscarmellose sodium | 0,200 kg |
| | Coloidal anhydrous silica | 0,050 kg |
| | Magnesium stearate | 0,050 kg |

I is mixed intimately in a highshear mixer, is wetted with
II and granulated into a moist mass. The moist granulate is dried in a fluid-bed dryer at an inlet air temperature of 60° C. until the dried granulate has a water activity of 0.3–0.4 (=in equilibrium with air of 30–40% R.H.).

The dried granulate is passed through a sieve with mesh openings of 850 micro meters.

The sieved granulate is finally mixed with III in a cone mixer.

The finished granulate is compressed into tablets of mass 1071 mg and sufficient hardness.

What we claim is:

1. A compound of the formula I

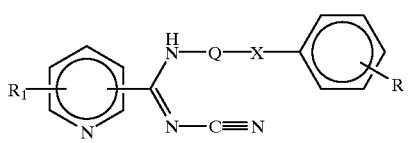

I or their tautomeric forms, the attachment to the pyridine being in the 2-, 3- or 4-position, in which formula $R_1$ stands for one or more substituents which can be the same or different and are selected from the group consisting of: hydrogen, halogen, amino, trifluoromethyl, nitro, cyano, carboxy, or alkyl, alkoxy, or alkoxycarbonyl, the C-content of which can be from 1 to 4; Q stands for $C_4$–$C_9$ divalent hydrocarbon radical which can be straight, branched, saturated or unsaturated; X stands for methylene, oxygen, sulphur or nitrogen, provided if X is methylene, then Q is $C_5$–$C_9$ divalent hydrocarbon radical which can be straight, branched, saturated or unsaturated, and R stands for hydrogen or for one or more substituents which can be the same or different and are selected from the group consisting of: hydroxy, amino, halogen, trifluoromethyl, cyano, nitro, carboxy, carbamoyl, methylenedioxy, or alkyl, alkoxy, alkylthio, alkylamino, or alkoxycarbonyl, the C-content of which can be from 1 to 4; and pharmaceutically acceptable, non-toxic salts and N-oxides thereof.

2. A compound according to formula I of claim 1, in which the attachment to the pyridine is in the 3-position, in which formula $R_1$ stands for hydrogen; Q stands for $C_4$–$C_9$ divalent hydrocarbon radical which can be straight, branched, saturated or unsaturated; X stands for methylene or oxygen, and R stands for hydrogen or for one or more substituents which can be the same or different and are selected from the group consisting of halogen, trifluoromethyl, cyano, nitro, carbamoyl, methylenedioxy, or alkyl, alkoxy, or alkoxycarbonyl, the C-content of which can be from 1 to 4; and pharmaceutically acceptable, non-toxic salts and N-oxides thereof.

3. A salt according to claim 1 in which the salt is selected from the group consisting of salts formed with hydrochloric, hydrobromic and hydroiodic acid, phosphoric acid, sulphuric acid, nitric acid, p-toluene-sulphonic acid, methanesulphonic acid, formic acid, acetic acid, propionic acid, citric acid, tartaric acid, and maleic acid, and lithium, sodium, potassium, magnesium, calcium salts, as well as salts with ammonia, $C_1$–$C_6$-alkylamines, $C_1$–$C_6$ alkanolamines, procaine, cycloalkylamines, and benzylamines.

4. A compound of claim 1 which is selected from the group consisting of:

$N^2$-Cyano-$N^1$-(6-(4-chlorophenoxy)hexyl)-3-pyridinecarboxamidine;

$N^2$-Cyano-$N^1$-(6-(2-methoxyphenoxy)hexyl)-3-pyridinecarboxamidine;

$N^2$-Cyano-$N^1$-(6-(3,4-methylenedioxyphenoxy)hexyl)-3-pyridinecarboxamidine;

$N^2$-Cyano-$N^1$-(6-(2-nitrophenoxy)hexyl-3-pyridinecarboxamidine;

and their salts and pure enantiomeric forms.

5. A pharmaceutical composition comprising a compound according to claim 1 together with a pharmaceutically acceptable carrier therefor.

6. A method of inhibiting the proliferation of cancer cells selected from lung carcinoma and breast cancer cells in a host which comprises administering to said host an effective amount of one or more compounds according to claim 1.

* * * * *